United States Patent [19]

Gilligan et al.

[11] Patent Number: 4,636,506

[45] Date of Patent: Jan. 13, 1987

[54] 7-HETEROCYCLIC-1,4-DIHYDROQUINO-LONES

[75] Inventors: Paul J. Gilligan, New Haven; Paul R. McGuirk, Gales Ferry, both of Conn.; Michael J. Witty, Dover, Great Britain

[73] Assignee: Pfizer, Inc., New York, N.Y.

[21] Appl. No.: 719,663

[22] Filed: Apr. 4, 1985

Related U.S. Application Data

[63] Continuation-in-part of Ser. No. 679,147, Dec. 6, 1984, abandoned.

[51] Int. Cl.$^4$ .................... A61K 31/47; C07D 215/18
[52] U.S. Cl. ................................. 514/256; 514/312; 544/333; 546/156
[58] Field of Search ............... 546/156; 514/312, 256; 544/333

[56] References Cited

U.S. PATENT DOCUMENTS

| | | | |
|---|---|---|---|
| 3,753,993 | 8/1973 | Lesher et al. | 260/286 R |
| 3,907,808 | 9/1975 | Lesher et al. | 260/287 R |
| 4,398,029 | 8/1983 | Irikura | 546/156 |
| 4,530,930 | 7/1985 | Uno | 546/156 |
| 4,544,658 | 10/1985 | Petersen | 546/156 |

*Primary Examiner*—Sidney Marantz
*Assistant Examiner*—Robert Benson
*Attorney, Agent, or Firm*—Charles J. Knuth; Peter C. Richardson; Gezina Holtrust

[57] ABSTRACT

1-Alkyl-6,8-difluoro-7-heterocyclic-1,4-dihydroquinol-4-one 3-carboxylic acids having antibacterial activity are prepared by conventional cyclization methods.

12 Claims, No Drawings

7-HETEROCYCLIC-1,4-DIHYDROQUINOLONES

CROSS REFERENCE TO RELATED APPLICATION

This application is a continuaton-in-part of Ser. No. 679,147 filed Dec. 6, 1984 now abandoned.

BACKGROUND OF THE INVENTION

This invention relates to 1-alkyl-6,8-difluoro-7-heterocyclic-1,4-dihydroquinol-4-one 3-carboxylic acids and their esters and cation salts, and the acid addition salts thereof, the preparation of said compounds, antibacterial compositions containing said compounds and a method of using said compounds.

Since the introduction of nalidixic acid in 1963, a considerable number of patents and scientific papers have been published on analogs of this compound. Representative of these publications are U.S. Pat. No. 3,753,993 describing compounds of the formula

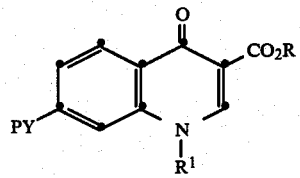

in which PY is 3- or 4-pyridyl, R may be hydrogen and $R_1$ may be short chain alkyl, and U.S. Pat. No. 3,907,808 disclosing compounds of the formula

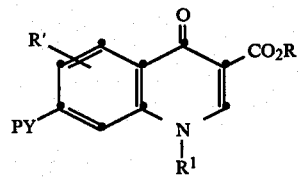

wherein R may be hydrogen, $R^1$ a short chain alkyl and PY is 2-,3- or 4-pyridyl which may be further substituted. R' of U.S. Pat. No. 3,907,808 is a substituent in the 5 or 6 position which may be halo. Compound 57A of the patent has a fluoro at the 6 position. Neither patent discloses 6,8-difluoro substitution.

SUMMARY OF THE INVENTION

The compounds of the present invention are of the formula

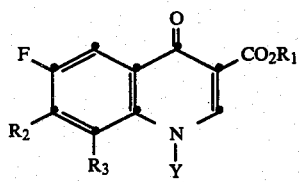

wherein
$R_1$ is hydrogen, a pharmaceutically acceptable cation or alkyl of 1 to 3 carbon atoms;
Y is selected from the group consisting of alkyl or haloalkyl of 1 to 3 carbon atoms, allyl, vinyl, cyclopropyl, hydroxyethyl, phenyl, 4-hydroxyphenyl and 4-fluorophenyl;

$R_2$ is 3-pyridyl or 4-pyridyl which may be substituted by one or two substituents selected from the group consisting of fluoro, chloro, hydroxy, alkoxy of 1 to 4 carbon atoms, amino, alkylamino of 1 to 4 carbon atoms, dialkylamino of 2 to 3 carbon atoms, carboxy, hydroxyalkyl of 1 to 6 carbon atoms, and aminoalkyl of 1 to 6 carbon atoms; 5-pyrimidinyl, or 6-quinolyl; and
$R_3$ is fluoro; or $R_3$ and Y when taken together have the formula

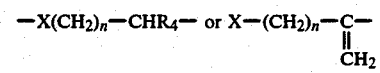

wherein
X is $CH_2$, O, S, NH or $NCH_3$,
n is 0, 1 or 2, and
$R_4$ is selected from the group consisting of hydrogen, alkyl and haloalkyl of 1 to 3 carbon atoms, hydroxymethyl, hydroxyethyl, aminomethyl and phenyl, and the acid addition salts thereof when $R_1$ is hydrogen.

Specific compounds of the invention are those wherein X is oxygen, n is 1 and $R_4$ is hydrogen.

Preferred compounds of the invention are those wherein $R_1$ is hydrogen or a pharmaceutically acceptable cation.

Other preferred compounds of the invention are those wherein Y is fluoroethyl or alkyl of 1 to 3 carbon atoms, preferably ethyl, and those wherein $R_2$ is 5-pyrimidinyl or 6-quinolyl.

Specific preferred compounds are 6,8-difluoro-7-(4-pyridyl)-1-ethyl-1,4-dihydroquinol-4-one 3-carboxylic acid, 6,8-difluoro-7-(3-pyridyl)-1-ethyl-1,4-dihydroquinol-4-one 3-carboxylic acid, 6,8-difluoro-7-(5-pyrimidyl)-1-ethyl-1,4-dihydroquinol-4-one 3-carboxylic acid, 6,8-difluoro-7-(6-quinolyl)-1-ethyl-1,4-dihydroquinol-4-one 3-carboxylic acid, 6,8-difluoro-7-(6-quinolyl)-1-fluoroethyl-1,4-dihydroquinol-4-one 3carboxylic acid, and the sodium and potassium salts of these acids.

The present invention also relates to antibacterial compositions comprising an antibacterially acceptable carrier and compound of formula I. Preferred compositions contain the preferred compounds of formula I as described above.

The invention further comprises a method of treating a host such as an animal or human being affected by a bacterial disease by administering to said host an antibacterially effective amount of a compound of formula I. Preferred methods of treatment administer a preferred compound of formula I as described above.

DETAILED DESCRIPTION OF THE INVENTION

The compounds of the invention may be prepared by known methods such as disclosed in Albrecht, R., Prog. Drug Res., Vol. 21 (1977) and illustrated in reaction Scheme A.

An N-substituted aniline of formula VII wherein $R_2$ and Y are as defined above is reacted with a dialkyl alkoxymethylene malonate of formula VIII wherein $R_5$ has from 1 to 6 carbon atoms. The reaction is generally carried out without solvent at about 100° to 200° C., preferably 150° to 175° C., for half an hour to 24 hours. The resulting intermediates of formula IX are crystallized from hydrocarbon solvents such as light petroleum or diethylether and cyclized by heating in polyphosphoric ester at about 100° to 200° C. for 15 minutes to 24 hours, preferably from 0.5 to 1 hour at 100° to 150° C. The resulting esters of formula I are usually purified by recrystallization or chromatography. Other methods of cyclization may be used such as described in Albrecht, R., Prog. Drug Res., Vol. 21, 35 (1977). Instead of polyphosphoric ester (also called polyphosphate ester), phosphorus oxychloride, phosphorus pentachloride, thionyl chloride, concentrated sulfuric acid or polyphosphoric acid may be used as listed on page 37 of Albrecht.

The compounds of formula X formed wherein $R_5$ is alkyl of 1 to 6 carbon atoms may be hydrolyzed to form the corresponding compounds wherein $R_5$ is hydrogen. The

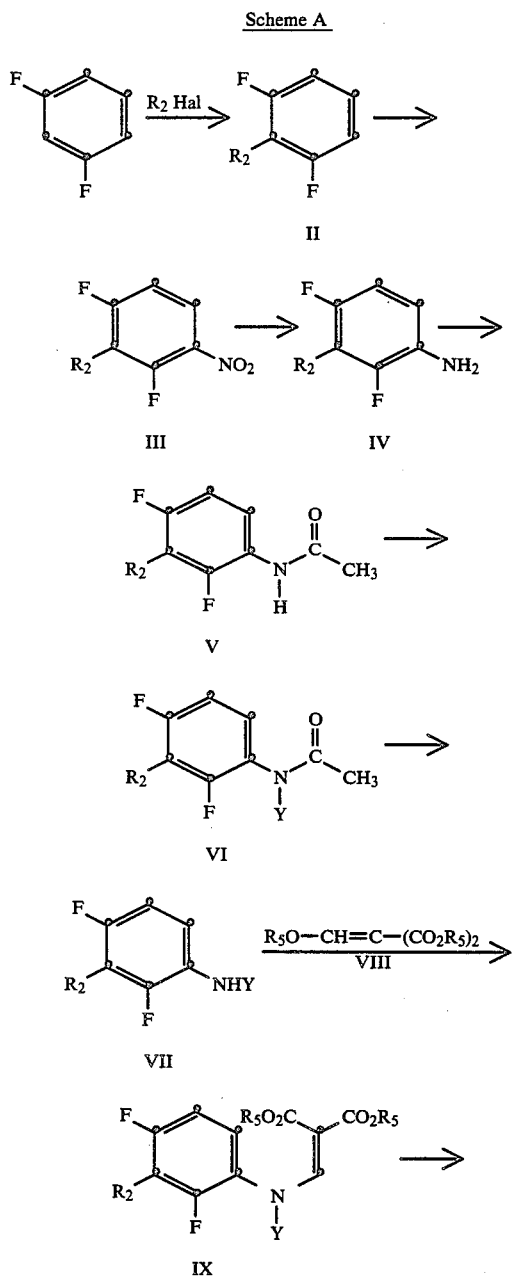

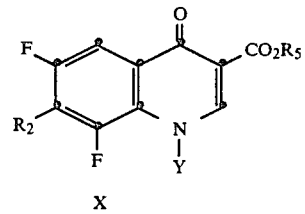

hydrolysis is by conventional methods, for instance by heating with an acid such as hydrochloric acid.

The N-substituted heteroarylanilines of formula VII may be prepared from the corresponding anilines of formula IV by conventional methods. For instance, an aniline of formula IV may be reacted with acetic anhydride in ethanol at 25° to 100° C. The formed compound of formula V is reacted with a suitable base such as sodium hydride and N-substituted with an appropriate halide, tosylate or mesylate containing group Y. The acetyl group in the formed compound of formula VI is removed by refluxing in aqueous media such as 6N hydrochloric acid to form the compound of formula VII.

Alternatively, N-substituted anilines of formula VII may be formed by reductive amination with an appropriate aldehyde and a suitable reducing agent such as diborane, palladium on carbon with hydrogen, sodium borohydride and sodium cyanoborohydride as for instance set out in March, J., Advanced Organic Chemistry, Second Edition, McGraw Hill, 819–820 (1977).

The heteroaryl-2,4-difluoroanilines of formula IV can be prepared from heteroaryl-2,4-difluorophenyls of formula II by standard nitration and subsequent reduction of the formed heteroaryl-2,4-difluoronitrophenyl compounds of formula III, as disclosed in the above March reference at pages 474 and 1125.

The compounds of formula II may be prepared by known methods such as disclosed in Klingsberg, E., Pyridine and its Derivatives, Part 2, 216–22 (1961), Abramovitch, R.A., Pyridine and its Derivatives, Supplement Part 2, 352–356 (1974), and Jones, G., Quinolines—The Chemistry of Heterocyclic Compounds, Part 1, 108–109 (1977). Most known methods convert a suitably substituted benzene derivative into the corresponding pyridyl-aryl compound by building up the pyridine ring. These methods often require a number of steps and are not readily adaptable to the preparation of substituted analogs.

According to a novel method described and claimed in copending application Ser. No. 679,148 filed Dec. 6, 1984 and assigned to the same assignee, the heteroaryl-2,4-difluorophenyls of formula II are prepared by transition metal catalyst coupling of difluorophenyl metal halides with haloheteroaryls of formula $R_2Hal$ wherein $R_2$ is as defined above and Hal is halogen. This method is shorter than prior art methods. The coupling reaction is suitably run in an ether solvent such as diethylether, dipropylether, tetrahydrofuran (THF) or dioxane, at temperatures of 25° to 50° C. The transition metal catalysts are known, e.g. from Negishi, E., Acc. Chem. Res., 15, 340–348 (1982) and references cited therein. Suitable transition metals are platinum, cobalt, iron, zirconium, molybdenum, ruthenium, manganese, rhodium, preferably, nickel, palladium and platinum. These metals are combined with ligands such as PPh$_3$, P(CH$_3$)$_3$, and P(C$_2$H$_5$)$_3$, wherein Ph is phenyl. Preferred transition metal catalysts are (PPh$_3$)$_4$Pd, (PPh$_3$)$_2$PdCl$_2$ and (PPh$_3$)$_4$Ni.

The difluorophenyl metal halides are usually prepared without isolation by reaction of meta-difluorobenzene with n-butyllithium at −78° to −50° C., preferably −78° to −70° C. in an ether solvent such as THF, and then with an anhydrous zinc halide such as zinc chloride at −78° to −50° C., preferably −78° to −70° C. The compound of formula R$_2$Hal such as 3-bromopyridine is added to the same reaction vessel alone or in an inert solvent, and the transition metal catalyst is added to the formed mixture. The catalyst is generally present in 0.1 to 10 mole %, preferably 5 mole %.

The compounds of formula I wherein R$_3$ and Y are taken together to form a ring may be prepared by the method set out in reaction Scheme B.

The compound of formula III is reacted with a compound of the formula HXCH$_2$CH$_2$OH wherein X is as defined above. Similarly, the compound of formula III may be reacted with a compound of formula HX(CH$_2$)$_n$CHR$_4$OH to obtain compounds of formula I wherein R$_4$ is other than hydrogen and n is 0, 1 or 2. The reaction is in an organic solvent such as THF at 0° C. to room temperature. When X is S, a base such as triethylamine has to be present. When X is O, an appropriately monoprotected diol is employed with sodium hydride as the base, For example, one eqivalent of t-butyldimethyl silylchloride is added to ethyleneglycol in DMF with imidazole to form the monoprotected diol. The protecting group may be suitably removed by tinchloride in ethanol during reduction of the nitro group. The ring closure reaction to compounds of formula XIV is carried out in the presence of azodicarboxylate and triphenylphosphine in THF at −5° C.

The compound of formula XI formed is reduced to the corresponding amine of formula XII by conventional reduction, e.g. as disclosed in the above March, J., reference at pages 474 and 1125.

The aniline of formula XII is reacted with a dialkyl alkoxymethylene malonate of formula VIII described above. In scheme B each of R$_4$ is hydrogen. The reaction proceeds as described above with reference to the conversion of a compound of formula VII in Scheme A. Subsequent ring closure to a compound of formula XV is as described above with reference to compounds of formula IX. Hydrolysis to XVI is by conventional methods, for instance by heating with an acid such as hydrochloric acid.

Scheme B

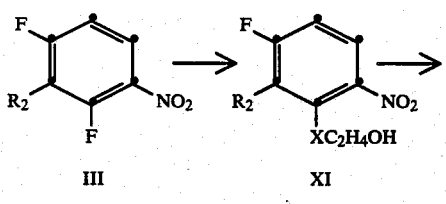

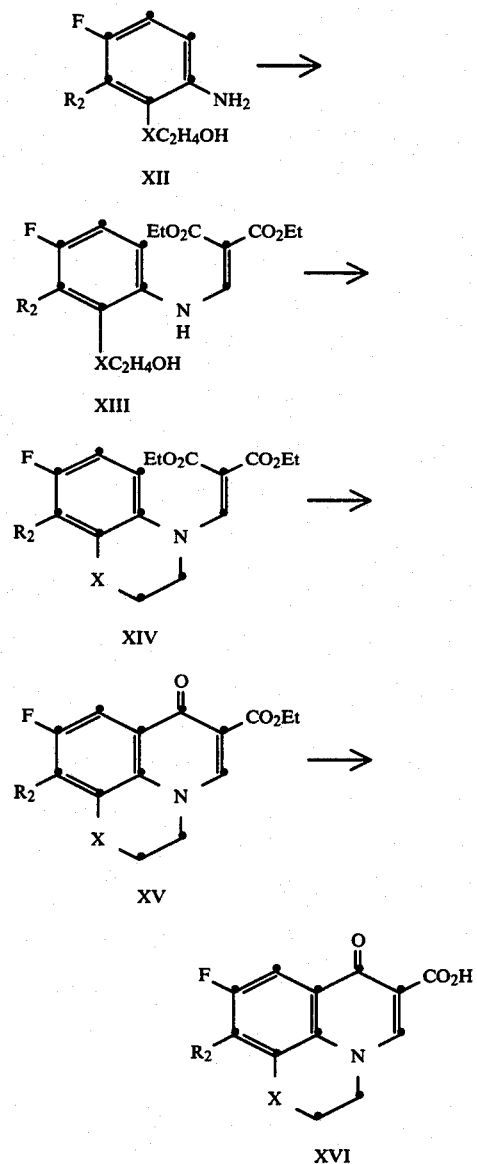

The pharmaceutically acceptable cation salts of the compounds of formula I may be prepared by conventional methods. For instance, the salts may be prepared by treating the compound of formula I in which R$_1$ is hydrogen with an aqueous solution of the desired pharmaceutically acceptable cation and evaporating the resulting solution to dryness, preferably under reduced pressure. Suitable pharmaceutically acceptable cations for this purpose include alkali metal salts such as potassium, sodium, and lithium salts, alkaline earth metal salts such as calcium and magnesium salts, ammonium salts and organic amine salts such as choline and diethanolamine salts.

The invention includes the acid addition salts of the compounds of formula I wherein R$_1$ is hydrogen and group R$_2$ has a nitrogen basic enough to be protonated with an acid. Particularly, pharmaceutically acceptable acid addition salts are included such as hydrochloric acid salts. These salts may be prepared in a conventional manner, e.g. by treating a solution or suspension of a compound of formula I with one chemical equivalent of an acid. Conventional concentration or crystallization techniques are employed in isolating the salts. Illustrative of suitable salts are those of acetic, lactic, succinic, maleic, tartaric, citric, gluconic, ascorbic, benzoic, cinnamic, fumaric, sulfuric, phosphoric, hydrochloric, sulfamic and sulfonic, such as methanesulfonic, benzenesulfonic and p-toluenesulfonic acids.

The sodium and potassium cation salts are preferred for parenteral administration because of their water solubility.

The compounds of the invention can be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5-1000 ppm, preferably 10-300 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.25-25 mg/kg/day, advantageously 0.5-10 mg/kg/day given in a single daily dose or up to 3 divided doses.

The invention also provides pharmaceutical compositions comprising an antibacterially effective amount of a compound of the formula (I) together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5-50 mg/kg/day given in a single dose or up to 3 divided doses. For intramuscular or intravenous administration, dosage levels are about 0.1-200 mg/kg/day, advantageously 0.5-50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The invention yet further provides a method of treating an animal, including a human being, having a bacterial disease which comprises administering to the animal an antibacterially effective amount of a compound of the formula (I) or a pharmaceutical composition as defined above.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The following examples illustrate the invention.

EXAMPLE 1

4-(2,6-Difluorophenyl)-pyridine

A. A 1.6 M solution of n-butyl lithium (14 ml) was added dropwise to a stirred solution of 1,3-difluorobenzene (2.17 g) in 34 ml dry tetrahydrofuran at $-78°$ C. After 1 hour at $-78°$ C., the solution was warmed to $-50°$ C. and a solution of anhydrous zinc chloride (3.0 g) in 34 ml tetrahydrofuran was added. After a further 30 minutes at $-50°$ C., a solution of 4-bromopyridine (1.62 g) in 10 ml ether was added followed by 1.0 g of tetrakis(triphenylphosphine) palladium. The solution was then allowed to warm slowly to room temperature and it was then heated at 40° C. for 12 hours. The mixture was cooled to room temperature and was first quenched with saturated aqueous ammonium chloride and then extracted with ethyl acetate. The organic extracts were dried and evaporated yielding a yellow crystalline solid. This material was purified by elution on silica gel with ethyl acetate/hexane to give 1.4 g (73% yield) of the required product as a pale yellow solid of m.p. 113°-114° C. NMR (CDCl3, 60 MHZ): 8.65 (m, 2H), 6.8-7.6 (m, 5H).

4-(2,6-Difluoro-3-nitrophenyl)-pyridine

B. A mixture of cold (0° C.) concentrated nitric acid (20.4 ml) and concentrated sulfuric acid (20.4 ml) was added in portions to a stirred solution of 10 g 4-(2,6-difluorophenyl)-pyridine in 56 ml concentrated sulfuric acid at 0° C. After 45 minutes at 0° C., the mixture was poured onto ice and the resulting solution was neutralized with solid sodium bicarbonate. It was then extracted twice with ethyl acetate and the organic extracts were dried and evaporated to give the product as white solid of m.p. 110°-112° C. (10.9 g, 88% yield). NMR (CDCl3, 60 MHz): 8.8 (m, 2H), 8.2 (m, 1H), 7.0-7.6 (m, 3H).

4-(3-Amino-2,6-difluorophenyl)-pyridine

C. A solution of 4-(2,6-difluoro-3-nitrophenyl)pyridine (10.9 g) in ethanol (500 ml) was hydrogenated (50 p.s.i.) for 1 hour over 15 g of Raney Nickel. The reaction mixture was then filtered through diatomaceus earth and the filtrate was evaporated in vacuo to give the product as a white solid of m.p. 190°-192° C. (6.6 g, 68% yield). NMR (DMSO d6, 250 MHz): 8.7 (m, 2H), 7.5 (m, 2H), 6.95 (m, 2H).

4-(3-Acetylamino-2,6-difluorophenyl)-pyridine

D. A mixture of 4-(3-amino-2,6-difluorophenyl)-pyridine (6.5 g), acetic anhydride (4.9 g) and ethanol (200 ml) was heated at reflux. After 1 hour, a further 3.3 ml acetic anhydride was added and a third portion (1.5 ml) after another 3.5 hours. Reflux was continued for a total of 6 hours after which time the solution was cooled and evaporated and the residue was partitioned between aqueous sodium bicarbonate and chloroform. The organic layer was washed with water, dried and evaporated to give the solid product of m.p. 148°-150° C. (6.8 g, 86% yield). NMR (CDCl3, 60 MHz): 8.8 (m, 2H), 8.05 (m, 2H), 7.4 (m, 2H), 6.9 (m, 1H), 2.2 (s, 3H).

N-Ethyl-2,4-difluoro-3-(4-pyridyl)-acetanilide

E. 4-(3-Acetylamino-2,6-difluorophenyl)-pyridine (6.8 g) was added portionwise to a stirred mixture of iodoethane (4.68 g) and 50% sodium hydride dispersion (1.44 g) in 65 ml N,N-dimethylformamide at 0° C. Once evolution of hydrogen was finished the mixture was stirred for 1 hour at room temperature. It was then poured onto iced water and the mixture was extracted twice with ethyl acetate. The combined organic extracts were washed with water, dried and evaporated, yielding the product as a solid of m.p. 119°–121° C. (6.6 g, 87% yield). NMR (CDCl3, 60 MHz): 8.65 (m, 2H), 7.5–7.0 (m, 4H), 3.6 (qt, 2H, J=6.5 Hz), 1.95 (s, 3H), 1.1 (t, 3H, J=6.5 Hz).

N-Ethyl 2,4-difluoro-3-(4-pyridyl)-aniline

F. A mixture of N-ethyl 2,4-difluoro-3-(4-pyridyl)acetanilide (6.6 g) and 60 ml 6M hydrochloric acid was heated at reflux for 2 hours. The mixture was cooled, extracted once with chloroform and the aqueous phase was neutralized with 30% aqueous sodium hydroxide. It was then extracted twice with chloroform and the combined organic extracts were dried and evaporated yielding the product as a pale brown oil (5.6 g) which was used immediately without further purification or characterization.

Diethyl 2,4-difluoro-(N-ethyl)-3-(4-pyridyl)anilinomethylene malonate

G. A mixture of 5.6 g of N-ethyl 2,4-difluoro-3-(4-pyridyl)-aniline and 5.19 g diethyl ethoxymethylene malonate was heated at 150° C. for 1 hour. The reaction mixture was then cooled and the resulting solid was washed well with petroleum ether to give the product as a pale brown solid of m.p. 104–106° C. (7.31 g, 75% yield). NMR (CDCl3, 250 MHz): 8.75 (d, 2H, J=5 Hz), 7.65 (s, 1H), 7.45 (m, 2H), 7.25 (m, 1H), 7.05 (m, 1H), 4.2 (qt, 2H, J=6 Hz), 3.75 (2qt, 4H, J=6 Hz), 1.25 (t, 6H, J=6 Hz), 1.1 (t, 3H, J=6 Hz).

Ethyl 1-ethyl-6,8-difluoro-7-(4-pyridyl)-1,4-dihydroquinol-4-one 3-carboxylate ($R_1$=ethyl; $R_2$=4-pyridyl; Y=ethyl)

H. A mixture of 35 ml polyphosphate ester and 3.5 g diethyl 2,4-difluoro-N-(ethyl)-3-(4-pyridyl)-anilinomethylene malonate was heated at 150° for 20 minutes. The reaction mixture was cooled, 100 ml water was added and the mixture was neutralized with solid sodium bicarbonate. This mixture was then stirred in the presence of excess sodium bicarbonate for 2 hours. The resulting precipitate was collected by filtration and washed well with water. It was then dissolved in chloroform and this solution was dried and evaporated yielding the product as a yellow solid (2.0 g, 65% yield). NMR (CDCl3, 250 MHz): 8.8 (m, 2H), 8.5 (s, 1H), 8.2 (dd, 1H, J=9 Hz and 2 Hz), 7.45 (m, 2H), 4.45 (2 qt, 4H), 1.45 (t, 3H, J=6 Hz), 1.35 (t, 3H, J=6 Hz).

1-Ethyl-6,8-difluoro-7-(4-pyridyl)-1,4-dihydroquinol-4-one 3-carboxylic acid ($R_1$=hydrogen; $R_2$=4-pyridyl; Y=ethyl)

I. A mixture of 1.28 g ethyl 1-ethyl-6,8-difluoro-7-(4-pyridyl)-1,4-dihydroquinol-4-one 3-carboxylic and 15 ml 2M hydrochloric acid was heated at reflux for 1 hour. The reaction mixture was then cooled in ice and the resulting precipitate was collected by filtration, washed with water, then ether and dried. The solid was dissolved in the minimum quantity of 1 M sodium hydroxide and the resulting solution was acidified with acetic acid. The precipitate was collected by filtration washed with water and dried, yielding the product as a white solid of m.p. 260° C. (1.22 g, 93% yield). NMR (DMSO d6/Trifluoroacetic acid d, 250 MHz): 9.2 (d, 2H, J=4.5 Hz), 9.1 (s, 1H), 8.4 (d, 2H, J=4.5 Hz), 8.2 (dd, 1H, J=7 Hz and 2 Hz), 4.7 (m, 2H), 1.5 (t, 3H, J=6 Hz).

Anal. calcd. for C17H12F2N20 3.0.25H20: C, 60.98, H, 3.74; N, 8.37%. Found: C, 60.60; H, 3.64; N, 8.21%.

1-Ethyl-6,8-difluoro-7-(4-pyridyl)-1,4-dihydroquinol-4-one 3-carboxylic acid sodium salt ($R_1$=sodium; $R_2$=4-pyridyl; Y=ethyl)

J. A mixture of 500 mg 1-ethyl-6,8-difluoro-7-(4-pyridyl)-1,4-dihydroquinol-4-one 3-carboxylic acid and 1.42 ml 1M sodium hydroxide in 20 ml water were stirred for 2 hours at room temperature. The solution was filtered and the water removed by freeze-drying yielding the product as a white solid of m.p. 285° C. (600 mg, 98.6% yield).

Analysis calculated or C17H11F2N203Na.2.25H20: C, 51.97; H, 3.94; N, 7.13%. Found: C, 51.77; H, 3.72; N, 7.01%.

EXAMPLE 2

3-(2,6-Difluorophenyl)-pyridine

A. The title compound was made by the method of Example 1A. 11.00 g (77% yield) were prepared from 1,3-difluorobenzene (12.8 g), anhydrous zinc chloride (20.48 g), 3-bromopyridine (11.85 g) and tetrakis(triphenylphosphine) palladium (5.0 g). The product is a pale yellow solid of m.p. 194°–196° C. NMR (CDCl3, 60 MHz): 9.1 (m, 2H), 7.0–8.4 (m, 5H).

3-(2,6-Difluoro-3-nitrophenyl)-pyridine

B. 9.13 g (56% yield) was prepared by the method of Example 1B. from 13.2 g of 3-(2,6-difluorophenyl)pyridine. The product is a white solid of m.p. 68°–70° C. NMR (CDCl3, 60 MHz): 8.8 (m, 2H), 8.2 (m, 1H), 7.0–7.6 (m, 3H).

3-(3-Amino-2,6-difluorophenyl)-pyridine

C. 7.1 g (90% yield was prepared by the method of Example 1C. from 3-(2,6-difluoro-3-nitrophenyl)-pyridine (9.0 g.). The product was a white solid of m.p. 112°–113° C.

3-(3-Acetylamino-2,6-difluorophenyl)-pyridine

D. 7.03 g (98% yield) was prepared by the method of Example 1D. from 3-(3-amino-2,6-difluorophenyl)-pyridine (6.5 g). M.p. 154.5°–155° C. NMR (CDCl3, 60 MHz): 8.65 (m, 2H), 6.8–8.5 (m, 4H), 2.3 (s, 3H).

N-ethyl 2,4-difluoro-3-(3-pyridyl)-acetanilide

E. 7.78 g (100% yield) of the title compound was prepared by the method of Example 1E from 3-(3-acetylamino-2,6-difluorophenyl)-pyridine (7.00 g). The brown oil formed was used directly without further purification. NMR (CDCl3, 60 MHz): 9.25 (m, 2H), 7.5–8.0 (m, 4H), 4.1 (qt, 2H, J=6.5 Hz), 2.3 (s, 3H), 1.6 (t, 3H, J=6.5 Hz).

N-Ethyl 2,4-difluoro-3-(3-pyridyl)-aniline

F. 7.08 g (92% yield) of the title compound was prepared by the method of Example 1F. from N-ethyl 2,4-difluoro-3-(3-pyridyl)-acetanilide (8.35 g). White solid of m.p. 79°–80° C. NMR (CDCl3, 60 MHz): 8.8 (m, 2H), 7.9 (m, 1H), 7.5 (m, 1H), 6.5–7.2 (m, 2H), 3.3 (qt, 2H, J=6.5 Hz), 1.5 (t, 3H, J=6.5 Hz).

Diethyl 2,4-difluoro-N-(ethyl)-3-(3-pyridyl)-anilinomethylene malonate

G. 8.9 g (75% yield) was made by the method of Example 1G. from 6.3 g N-ethyl 2,4-difluoro-3-(3-pyridyl)aniline. M.P. 72.5°–74.5° C. NMR (CDCl3, 60 MHz): 8.8 (m, 2H), 8.1 (m, 1H), 7.8 (s, 1H), 7.7–7.0 (m, 3H), 4.4 (qt, 2H, J=6.5 Hz), 3.9 (2 qt, 4H, J=6.5 Hz), 1.5 (t, 6H, J=6.5 Hz), 1.4 (t, 3H, J=6.5 Hz).

Ethyl 1-ethyl-6,8-difluoro-7-(3-pyridyl)-1,4-dihydroquinol-4-one 3-carboxylate ($R_1$=ethyl; $R_2$=3-pyridyl, Y=ethyl)

H. 0.88 g (26% yield) of the title compound was made by the method of Example 1H. from 1.00 g 2,4-difluoro-N-ethyl-3-(3-pyridyl)-anilinomethylene malonate as a yellow solid of m.p. 141°–143° C. NMR (CDCl3, 250 MHz): 8.75 (m, 2H), 8.45 (s, 1H), 8.2 (d, 1H, J=9 Hz), 7.8 (m, 1H), 7.5 (m, 1H) 4.4 (2 q, 4H), 1.5 (t, 3H, J=6.5 Hz), 1.4 (t, 3H, J=6.5 Hz).

1-Ethyl-6,8-difluro-7-(3-pyridyl)-1,4-dihydroquinol-4-one 3-carboxylic acid hydrochloric salt ($R_1$=hydrogen; $R_2$=3-pyridyl; Y=ethyl)

I. A mixture of ethyl 1-ethyl-6,8-difluoro-7-(3-pyridyl)-1,4-dihydroquinol-4-one 3-arboxylate (1.1 g) and 20 ml 2 M hydrochloric acid was heated at reflux for 0.5 hours. The reaction mixture was cooled and the resulting precipitate was collected by filtration, washed with water and dried, yielding the product as a white solid of m.p. 270° C. 930 mg, 85% yield). NMR (DMSO d6/Trifluoroacetic acid d, 250 MHz): 9.3 (m, 2H), 9.1 (d, 1H, J=6 Hz), 8.95 (d, 2H, J=7 Hz), 8.4 (m, 1H), 4.95 (m, 2H), 1.7 (t, 3H, J=6 Hz).

1-Ethyl-6,8-difluoro-7-(3-pyridyl)-1,4-dihydroquinol-4-one 3-carboxylic acid sodium salt J. A mixture of 1.12 g 1-ethyl-6,8-difluoro-7-(3-pyridyl)-1,4-dihydroquinol-4-one 3-carboxylic acid hydrochloride and 6.25 ml 1M sodium hydroxide in 8 ml water were stirred for 1 hour at room temperature. The solution was filtered and the water was removed by evaporation in vacuo yielding the product as a white solid of m.p. 290°–295° C. (1.4 g, 88% yield).

Anal. calcd. for C17H11F2N2O3Na.NaCl.6H2O: C, 39.34; H, 4.43; N, 5.40%. Found: C, 39.62; H, 2.53; N, 5.10%.

EXAMPLE 3

N-Acetyl-N-(2'-fluoroethyl)-2,4-difluoro-3-(4'-pyridyl)aniline

A. Sodium hydride (0.85 g, 50% in oil, 17.7 mmol) was washed with hexanes twice. The washings were decanted. Dimethylformamide (40 ml) was added with stirring. 1-Bromo-2-fluoroethane (2.24 g, 1.3 ml, 17.6 mmol) was added and the reaction mixture was cooled to 0° C. N-Acetyl-2,4-difluoro-3-(4'-pyridyl)aniline (4 g, 16 mmol) was added in portions. The reaction mixture was warmed gradually to room temperature. After 2 hours, the reaction mixture was cooled again to 0° C. and more sodium hydride (0.19 g, 8 mmol, prewashed with hexanes) and more 1-bromo-2-fluoroethane (1.12 g, 0.6 ml, 8.8 mmol) were added. The reaction mixture was warmed gradually to room temperature and stirred for 2 hours. The mixture was poured onto ice-water and the resulting mix was extracted twice with ethyl acetate. The combined organic layers were washed four times with water, dried over magnesium sulfate and filtered. Solvent was removed in vacuo to afford a solid (3.93 g, 84% yiled): m.p. 125°–128° C.; NMR (60 MHz, CDCl3): 8.8–8.6 (m, 2H), 7.5–7.0 (m, 4H), 5.1–4.9 (m, 1H), 4.4–3.5 (m, 3H), 1.9 (s, 3H).

2,4-Difluoro-N-(2'-fluoroethyl)-3-(4'-pyridyl)aniline

B. N-Acetyl-N-(2'-fluoroethyl)-2,4-difluoro-3-(4'-pyridyl)aniline (4.16 g, 14.7 mmol) was added to a 6N hydrochloric acid solution (40 ml) with stirring. The reaction mixture was heated to reflux for 2 hours. The mixture was then cooled to 0° C. and made basic by adding a 30% sodium hydroxide solution (final pH=8 by test paper). Three extractions with chloroform, drying the combined organic layers over magnesium sulfate, filtration and drying in vacuo afforded a brown oil (3.5 g): MS: Calcd for C13H11F3N2: 252.0874, Found: 252.0872.

Diethyl N-(2',4'-Difluoro-3-(4''-pyridyl)phenyl)-N-(2'-fluoroethyl)aminomethylenepropane-1,3-dioate C. A mixture of 2,4-difluoro-N-(2'-fluoroethyl)-3-(4'-pyridyl)aniline (3.53 g, 14 mmol) and diethyl ethoxymethylenemalonate (3.03 g, 2.8 ml, 14 mmol) was heated at 150° C. for 2 hours. The reaction mixture was cooled to room temperature. Flash chromatography (ethyl acetate) afforded after removal of solvent, an oil (1.2 g, 20% yield): NMR (60 MHz, CDCl3): 8.7–8.5 (m, 2H), 7.6 (s, 1H), 7.5–6.7 (m, 4H), 4.9 (t, 1H, J=6 Hz), 4.4–3.4 (m, 7H), 1.2 (t, 3H, J=7 Hz), 1.0 (t, 3H, J=7 Hz). MS: Cald for C21H21F3N2O4: 422.1453; Found: 422.1451.

Ethyl 6,8-Difluoro-1-(2'-fluoroethyl)-7-(4'-pyridyl)-1,4-dihydroquinol-4-one-3-carboxylate D. A mixture of diethyl N-(2',4'-difluoro-3-(4''-pyridyl)phenyl)-N-(2'-fluoroethyl)aminomethylenepropane-1,3-dioate (1.2 g, 2.8 mmol) and polyphosphoric acid ethyl ester (12 ml) were heated at 150° C. with stirring for 30 minutes. The reaction mixture was poured onto a saturated sodium bicarbonate solution with stirring. Solid sodium bicarbonate was added to keep the mixture alkaline (pH=8 by test paper). The aqueous mixture was extracted three times with chloroform. The combined organic layers were dried over magnesium sulfate and filtered. Solvent was removed in vacuo to afford an oil. Trituration with ether afforded a solid (88 mg): m.p. 250° C.; NMR (CDCl3, 250 MHz): 8.90–8.65 (m, 2H), 8.45 (s, 1H), 8.20 (dd, 1H, J=7, 1 Hz), 7.50–7.30 (m, 2H), 4.90–4.60 (m, 4H), 4.45 (q, 2H, J=7. Hz), 1.45 (t, 3H, J=7. Hz).

6,8-Difluoro-1-(2'-fluoroethyl)-7-(4'-pyridyl)-1,4-dihydroquinol-4-one 3-carboxylic acid ($R_1$=hydrogen; $R_2$=4-pyridyl; $R_3$=F; Y - 2-fluoroethyl)

E. A mixture of diethyl 6,8-difluoro-1-(2'-fluoroethyl)-7-(4'-pyridyl) 1,4-dihydroquinol-4-one-3-carboxylate (80 mg. 0.21 mmol) and 2N hydrochloric acid solution (2 ml) was heated at reflux temperature for 1 hour. The reaction mixture was cooled to ambient temperature and neutralized with a standard sodium bicarbonate solution. The precipitate was filtered and washed with water. Drying in vacuo afforded a solid (40 mg): m.p. 250° C.; NMR (250 MHz, CF3CO2D): 9.25 (s, 1H), 9.20–9.05 (m, 2H), 8.55–8.30 (m, 3H), 5.35–4.85 (m, 4H).

EXAMPLE 4

6-(2,6-Difluorophenyl)-quinoline

A. A 1.55 M solution of n-butyllithium (40 ml) in hexanes was added dropwise to a stirred solution of 1,3-difluorobenzene (5.7 g) in 150 ml of dry tetrahydrofuran at −78° C. After one hour at −78° C. a solution of anhydrous zinc chloride (10.22 g) in 40 ml of tetrahydrofuran was added. After a further 10 minutes at −78° C., 9.36 g (45 mmoles) 6-bromoquinoline was added neat followed by tetrakistriphenylphosphine palladium (2.5 g, 2.16 mmoles). The solution was then allowed to warm slowly to room temperature and heated to 40° C. for 12 hours. The mixture was cooled to room temperature and quenched with saturated aqueous ammonium chloride. The pH was adjusted to 9 and the product was extracted with ethyl acetate, dried over $MgSO_4$; filtered and concentrated in vacuo to give a white solid (9.5 g, 88%) of m.p. 112°–113° C.

NMR (DMSO-$d_6$, 250 MHz): 9.00 (m, 1H), 8.48 (d, 1H), 8.15 (m, 2H), 7.85 (d, 1H), 7.55 (m, 2H), 7.30 (t, 2H).

6-(2,6-Difluoro-3-nitrophenyl)-quinoline

B. The title compound was prepared by the method of Example 1B. A 5.00 g sample (70% yield) was made from 6-(2,6-difluorophenyl)-quinoline (6.02 g, 25 mmoles) and 50 ml of concentrated $H_2SO_4$ and 1.5 ml of concentrated $HNO_3$. The product was isolated as an off white solid of m.p. 152°–153° C. NMR (DMSO-$d_6$, 250 MHz): 9.05 (d of d, 1H), 8.50 (d, J=5 Hz, 1H), 8.40 (sextet, 1H), 8.24 (s, 1H), 8.20 (d, J=5.0 Hz, 1H), 7.87 (d, J=5.0 Hz, 1H), 7.60 (m, 2H).

6-(3-Amino-2,6-difluorophenyl)-quinoline

C. A solution of 6-(3-amino-2,6-difluorophenyl)-quinoline (5.70 g, 20.0 mmoles) in 300 ml of absolute ethanol was treated with stannous chloride dihydrate (22.5 g, 100 mmoles). The mixture was heated to 70° C. for 2 hours, cooled to room temperature, and poured onto ice water and saturated aqueous sodium bicarbonate. The pH of the mixture was adjusted to 13 with 6N NaOH. The product was then extracted with ethyl acetate. The organic phase was washed with water and saturated aqueous sodium chloride, dried over $MgSO_4$, filtered and evaporated to give 3.6 g (70% yield) of a light yellow solid after chromatography on silica gel (ethylacetate/hexanes), m.p. 178°–179° C.

NMR (DMSO-$d_6$, 250 MHz): 8.99 (d of d, 1H), 8.48 (d, J=6.5 Hz, 1H), 8.15 (d, J=9.5 Hz, 1H), 8.10 (s, 1H), 7.80 (d, J=6.5 Hz, 1H), 7.60 (d of d, J=5.0 Hz, 1H), 6.95 (t, J=9.5 Hz, 1H), 6.85 (sextet, 1H), 5.15 (s, 2H).

Diethyl 2,4-difluoro-3-(6-quinolyl)anilinomethylene malonate

D. A mixture of 6-(3-amino-2,6-difluorophenyl)-quinoline (4.0 g, 15.6 mmoles) and diethyl ethoxymethylene malonate (3.37 g, 15.6 mmoles) was heated at 150° C. for 2 hours. The reaction mixture was cooled to room temperature and the resulting solid was triturated with petroleum ether, and chromatographed on silica gel (ethyl acetate-hexanes) to give 6.0 g (90% yield) of a light tan solid of m.p. 84°–85° C.

NMR (DMSO-$d_6$, 250 MHz): 10.95 (br d, J=13.0 Hz, 1H), 9.11 (d, J=3.9 Hz, 1H), 8.50 (m, 2H), 8.18 (d, 2H), 7.90 (d, J=7.7 Hz, 1H), 7.80 (sextet, 1H), 7.65 (d of d, J=3.9 Hz, 1H), 7.37 (t, J=7.5 Hz, 1H), 4.20 (six line multiplet, 4H), 1.25 (t, J=7.0 Hz, 6H).

Ethyl 6,8-difluoro-7-(6-quinolyl)quinoline-4-ol 3-carboxylic acid

E. A solution of diethyl 2,4-difluoro-3-(6-quinolyl)anilinomethylene malonate (5.90 g, 13.8 mmoles) in 60 ml of Dowtherm A was heated to 210° C. for 3 hours. The solution was cooled to room temperature and diluted with hexanes. The resulting precipitte was collected by suction filtration and washed successively with ethyl acetate, chloroform, acetone and diethyl ether to give 4.55 g (87% yield) of a tan solid. M.p. 284°–286° C.

NMR (DMSO-$d_6$/TFA-d, 250 mHz): 9.45 (s, 1H), 9.30 (d, 2H), 8.62 (s, 1H), 8.60 (d, 1H), 8.40 (d, 1H), 8.30 (d of d, 1H), 8.25 (m, 1H), 4.65 (q, J=7.0 Hz, 2H), 1.52 (t, J=7.0 Hz, 3H).

Ethyl 7-(6-quinolyl)-6,8-difluoro-1-ethyl-1,4-dihydroquinol-4-one 3-carboxylic acid F. To a suspension of ethyl 7-(6-quinolyl)-6,8-difluoroquinoline-4-ol 3-carboxylic acid (4.50 g, 11.8 mmoles) and potassium carbonate (10 g, 72.5 mmoles) in 75 ml of dry DMF was added iodoethane (3.69 g, 23.7 mmoles). The reaction mixture was heated to 100° C. for 12 hours, cooled to room temperature and poured into water. The aqueous phase was extracted with ethyl acetate. The organic phase was washed with water and saturated aqueous sodium chloride, dried over $MgSO_4$ and filtered. The light tan solid obtained upon evaporation was triturated with diethyl ether to yield 2.75 g (57% yield). M.p. 184°–185° C.

NMR (DMSO-$d_6$, 250 MHz): 9.05 (m, 1H), 8.75 (s, 1H), 8.50 (d, J=8.4 Hz, 1H), 8.25 (s, 1H), 8.20 (d, J=12.5 Hz, 1H), 7.95 (t, J=12.5 Hz, 2H), 7.68 (d of d, J=5.0 Hz, 1H), 4.51 (m, 2H), 4.29 (q, J=7.0 Hz, 2H), 1.45 (t, J=7.0 Hz, 3H), 1.25 (t, J=7.0 Hz, 3H).

6,8-Difluoro-1-ethyl-7-(6-quinolyl)-1,4-dihydroquinol-4-one 3-carboxylic acid G. To ethyl 6,8-difluoro-1-ethyl-7-(6-quinolyl)-1,4-dihydroquinol-4-one 3-carboxylic acid (2.75 g, 6.74 mmoles) was added 100 ml of 1 N HCl. The suspension was heated to reflux. The clear solution obtained was heated for 4 hours and a precipitate formed. The mixture was cooled to room temperature and filtered. The air dried solid was then washed with ethyl acetate and recrystallized from hot DMF to give 2.34 g (91% yield) of an off-white solid. M.p. 281°–282° C.

NMR (DMSO-$d_6$, 250 MHz): 9.12 (d of d, 1H), 9.10 (s, 1H), 8.65 (d, 1H), 8.35 (s, 1H), 8.25 (d, 1H), 8.15 (d of d, 1H), 8.05 (d, 1H), 7.75 (d of d, 1H), 4.68 (m, 2H), 1.48 (t, J=7.0 Hz, 3H).

EXAMPLE 5

Ethyl 6,8-difluoro-1-ethyl-7-(6-quinolyl)-1,4-dihydroquinol-4-one 3-carboxylic acid ($R_1$=ethyl; $R_2$=6-quinolyl; $R_3$=fluoro; Y=ethyl)

A. To 300 ml of dry THF was added 6-bromoquinoline (4.16 g, 20 mmoles) and the solution was cooled to −100° C. with a liquid nitrogen/isopropanol/methanol bath. To the solution was added 20 ml of 2M t-butyllithium in pentane and zinc chloride (6.13 g, 45 mmoles) in THF. The temperature was allowed to warm to −50° C. and ethyl 7-bromo-6,8-difluoro-1-ethyl-1,4-dihydroquinol-4-one 3-carboxylic acid (5.40 g, 15 mmoles) was added, followed by addition of tetrakistriphenylphosphine palladium (2.50 g, 2.16 mmoles). The dark yellow reaction mixture was heated to 45° C. for 12 hours. The resulting reddish-brown solution was cooled to room temperature and poured into water. The aqueous phase was extracted with chloroform. The organic phase was then washed once with saturated aqueous ammonium chloride and twice with distilled water. The organic phase was dried over MgSO$_4$, filtered and concentrated in vacuo. The crude concentrate was chromatographed on silica gel with ethyl acetate. The solids obtained were triturated with diethyl ether to give 2.5 g (41% yield) of a white solid of m.p. 186°–187° C. The NMR and high resolution mass spectra were identical to those obtained for Example 4F.

6,8-Difluoro-1-ethyl-7-(6-quinolyl)-1,4-dihydroquinol-4-one 3-carboxylic acid B. The above ethyl ester (2.4 g, 5.88 mmoles) was hydrolyzed according to the method of example 4G to give 2.10 g (94% yield) of a white solid. The solid obtained was dissolved in water by the addition of 1N KOH until pH=8.5. The free base was then precipitated from solution by the addition of glacial acetic acid. The precipitate was collected by suction filtration, air dried and recrystallized from hot acetonitrile to give a white crystalline solid of m.p. 284°–285° C.

Anal: Calcd. for $C_{21}H_{14}O_3N_2F_2$: C, 66.32; H, 3.68; N, 7.37%. Found: C, 66.18; H, 3.84; N, 7.20%.

The NMR and high resolution mass spectra were identical to those obtained for Examples 4G.

EXAMPLE 6

5-(2,6-Difluorophenyl)-pyrimidine

A. The title compound was made by the method of Example 4A. A 7.5 g sample (82% yield) was prepared from 1,3-difluorobenzene (10.8 g, 95 mmoles), n-butyllithium (47 ml, 112.8 mmoles), anhydrous zinc chloride (15.64 g, 116 mmoles), 5-bromopyrimidine (7.60 g, 48 mmoles) and tetrakis(triphenylphosphine) palladium (2.50 g, 2.16 mmoles). The product is a pale yellow solid of m.p. 67°–69° C. (hexanes/benzene).

NMR (CDCl$_3$, 250 MHz): 9.20 (s, 1H), 8.85 (d, 2H), 7.38 (m, 1H), 7.05 (m, 2H).

5-(2,6-Difluoro-3-nitrophenyl)-pyrimidine

B. A 7.70 g sample (84% yield) was prepared by the method of Example 4B, from 5-(2,6-difluorophenyl)-pyrimidine (7.50 g, 39.1 mmoles). The product is a tan solid of m.p. 78°–80° C. (hexanes/benzene).

NMR (CDCl$_3$, 250 MHz): 9.30 (s, 1H), 8.88 (m, 2H), 8.24 (six line multiplet, 1H), 7.24 (seven line multiplet, 1H).

5-(3-Amino-2,6-difluorophenyl)-pyrimidine

C. A 5.30 g sample (91% yield) was prepared by the method of Example 4C from 3-(2,6-difluoro-3-nitrophenyl)pyrimidine (6.70 g, 28.3 mmoles). The product was a light tan solid of m.p. 141°–143° C. NMR (CDCl$_3$, 250 MHz): 9.21 (s, 1H), 8.86 (m, 2H), 6.83 (complex multiplet, 2H), 3.78 (br s, 2H).

Diethyl 2,4-difluoro-3-(5-pyrimidyl)anilinomethylene malonate

D. 10.59 G (95% yield) was made by the method of Example 3D from 5-(3-amino-2,5-difluorophenyl)-pyrimidine (6.12 g, 29.6 mmoles). The product was purified by column chromatography on silica gel (ethyl acetate/hexanes, 1% triethylamine) to give a white solid of m.p. 111°–115° C. (methanol).

NMR (CDCl$_3$, 250 MHz): 11.1 (br d, J=13.5 Hz, 1H), 9.24 (s, 1H), 8.88 (m, 2H), 8.42 (d, J=13.5 Hz, 1H), 7.35 (m, 1H), 7.12 (t of d, 1H), 4.29 (six line multiplet, 4H), 1.34 (six line multiplet, 6H).

Ethyl 6,8-difluoro-7-(5-pyrimidyl)-quinoline-4-ol 3-carboxylate

E. 4.26 g (88% yield) of the title compound was prepared by the method of Example 4E from diethyl 2,4-difluoro-3-(5-pyrimidyl)-anilinomethylene malonate (5.50 g, 14.6 mmoles). The product is a brown solid of m.p. 280°–285° C.

NMR (TFA-d/DMSO-d$_6$, 250 MHz): 9.59 (s, 1H), 9.39 (s, 2H), 9.35 (s, 1H), 8.25 (d of d, 1H), 4.60 (q, J=7.0 Hz, 2H), 1.49 (t, J=7.0 Hz, 3H).

Ethyl 1-ethyl-6,8-difluoro-7-(5-pyrimidyl)-1,4-dihydroquinol-4-one 3-carboxylic acid F. A 0.23 g sample (38% yield) was prepared from ethyl 6,8-difluoro-7-(5-pyrimidyl)-quinoline-4-ol 3-carboxylate (0.50 g, 1.51 mmoles) by the method of Example 4F. A pale yellow solid of m.p. 160°–162° C. (ethyl acetate) was obtained.

NMR (CDCl$_3$, 250 MHz): 9.30 (s, 1H), 8.90 (m, 2H), 8.45 (s, 1H), 7.20 (d of d, 1H), 4.42 (m, 4H), 1.56 (t, J=7.0 Hz, 3H), 1.42 (t, J=7.0 Hz, 3H).

1-Ethyl 6,8-difluoro-7-(5-pyrimidyl)-1,4-dihydroquinol-4-one 3-carboxylic acid ($R_1$=hydrogen; $R_2$- 5-pyrimidyl; $R_3$=F; Y=ethyl)

G. A 1.02 g sample (77% yield) of the title compound was prepared from ethyl 1-ethyl-6,8-difluoro-7-(5-pyrimidyl)-1,4-dihydroquinol-4-one 3-carboxylate (1.44 g, 4.01 mmoles) by the method of Example 4G. The product is a white crystalline solid of m.p. 317°–319° C.

NMR (TFA-d/DMSO-d$_6$, 250 MHz): 9.82 (s, 1H), 9.65 (s, 2H), 9.30 (s, 1H), 8.41 (d of d, 1H), 4.95 (br m, 2H), 1.72 (t, J=7.0 Hz, 3H).

EXAMPLE 7

2-(2-Hydroxyethyl)thio-3-(3'-pyridyl)-4-fluoronitrobenzene

A. A solution of 2,4-difluoro-3-(3'-pyridyl)-nitrobenzene (3.11 g, 13.2 mmoles) in 50 ml of THF at room temperature was treated with 2-mercaptoethanol (3.09 g, 39.6 mmoles) and triethylamine (10 ml). After 2.5 hours the solution was diluted with water and extracted with ethyl acetate. The organic layer was washed three times with water and one time with saturated aqueous sodium chloride, dried over MgSO$_4$, filtered and concentrated in vacuo. The crude concentrate was chromatographed on silica gel (ethyl acetate) to give 3.6 g (93% yield) of a pale yellow oil.

NMR (CDCl$_3$, 250 MHz): 8.65 (m, 2H), 7.80 (d, J=6.3 Hz, 1H), 7.70 (d of d, J=3.5 Hz, 1H), 7.46 (d of d, J=3.5 Hz, 1H), 7.30 (t, J=6.3 Hz, 1H), 3.48 (t, J=6.3 Hz, 2H), 2.50 (t, J=6.3 Hz, 2H).

2-(2-Hydroxyethyl)thio-3-(3'-pyridyl)-4-fluoroaniline

B. To a solution of 2-(2-hydroxyethyl)thio-3-(3'-pyridyl)-4-fluoronitroenzene (3.61 g, 12.2 mmoles) in 75 ml of absolute ethanol was added stannous chloride dihydrate (13.8 g, 61.4 mmoles). The resulting yellow suspension was heated to 70° C. for 30 minutes, cooled to room temperature and poured onto ice water. The pH was adjusted to 14 with saturated aqueous sodium bicarbonate and then 1N sodium hydroxide. The aqueous phase was extracted with ethyl acetate. The organic phase was dried over MgSO$_4$, filtered and concentrated in vacuo to give 2.64 g (82% yield) of a light tan solid of m.p. 133°–134° C.

Diethyl N-(2-(2-hydroxyethyl)thio 3-(3'-pyridyl)-4-fluorophenyl)-N-aminomethylene propane-1,3-dioate C. A mixture of 2-(2-hydroxyethyl)thio-3-(3'-pyridyl)-4-fluoroaniline (2.65 g, 10.0 mmoles) and diethylethoxymethylene malonate (2.16 g, 10.0 mmoles) and ethanol was heated to 130° C. for 20 minutes. The reaction mixture was cooled to room temperature and diluted with ethyl acetate. The solution was chromatographed on silica gel (ethylacetate - 1% triethylamine) to give 3.59 g (82% yield) of a light yellow oil which solidified on standing. M.p. 109°–112° C.

NMR (CDCl$_3$, 250 MHz): 11.9 (d, J=10.4 Hz, 1H), 8.68 (m, 1H), 8.60 (s, 1H), 7.72 (d, 1H), 7.40 (m, 4H), 4.32 (m, 4H), 3.46 (q, 2H), 2.50 (t, 2H), 1.32 (m, 6H).

2-(8-Fluoro-7-(3'-pyridyl)-2,3-dihydro-4H-1,4-benzothiazine-4-yl) methylene malonic acid diethyl ester D. To a mixture of triphenylphosphine (3.25 g, 12.4 mmoles) and ethyl azodicarboxylate (2.15 g, 12.4 mmoles) in THF at −20° C. was added diethyl-N-(2-(2-hydroxyethyl)thio-3-(3'-pyridyl)-4-fluorophenyl-N-aminomethylenepropane-1,3-dioate (3.59 g, 8.27 mmoles) as a solution in THF. The mixture was warmed to room tempeature, diluted with water and extracted with ethyl acetate. The organic phase was dried over MgSO$_4$, filtered and concentrated in vacuo. The crude mterial was chromatographed on silica gel (ethyl acetate/hexanes −1% triethylamine) to afford 2.57 g (75% yield) of a yellow oil which crystallized on standing. M.p. 44°–47° C.

NMR (CDCl$_3$, 250 MHz): 8.66 (d of d, 1H), 8.55 (d, 1H), 7.70 (s, 1H), 7.65 (m, 1H), 7.40 (d of d of d, 1H), 7.10 (d of d, 1H), 6.96 (t, J=8.9 Hz, 1H), 4.21 (q, 2H), 4.15 (q, 2H), 3.80 (m, 2H), 3.05 (m, 2H), 1.28 (two overlapping triplets, 6H).

9-Fluoro-10-(3'-pyridyl)-7-oxo-2,3-dihydro-7H-pyrido[1,2,3-de] [1,4] benzothiazine-6-carboxylic acid ethyl ester E. A mixture of diethyl-N-(2-(2-hydroxyethyl)thio-3-(3'-pyridyl)-4-fluorophenyl)-N-aminomethylenepropane-1,3-dioate (1.85 g, 4.45 mmoles) and polyphosphte ester (20 ml) was heated to 130°–145° C. for 30 minutes. The clear dark solution was cooled to 0° C. and poured onto ice/saturated aqueous NaHCO$_3$. The pH was adjusted to 7.5 with additional sodium bicarbonate and the mixture was stirred at room temperature for 2 hours. The solid precipitate was collected by suction filtration and air dried to provide 1.30 g (79% yield) of a light tan solid of m.p. 235°–237° C.

NMR (CDCl$_3$, 250 MHz): 8.69 (d, J=5.0 Hz, 1H), 8.58 (s, 1H), 8.35 (s, 1H), 7.94 (d, J=7.6 Hz, 1H), 7.70 (d of t, J=7.6 Hz, 1H), 7.45 (d of d, J=4.8 Hz, 1H), 4.49 (m, 2H), 4.35 (q, J=6.4 Hz, 2H), 3.28 (m, 2H), 1.40 (t, J=6.4 Hz, 3H).

9-Fluoro-10-(3'-pyridyl)-7-oxo-2,3-dihydro-7H-pyrido[1,2,3-de][1,4]benzothiazine-6-carboxylic acid. (R$_1$=hydrogen; R$_2$=3-pyridyl; X=S; R$_4$=hydrogen; n=1)

F. A mixture of the ethyl ester from example 7E, (525 mg, 1.42 mmoles), 1N sodium hydroxide (3 ml) and THF (1 ml) was heated to 100° C. for 2 hours, a dark brown solution resulted. After evaporation of the remaining THF and cooling to room temperature a solid mass formed, which was treated with water and 6N HCl until pH 2. The solids were collected by suction filtration, air dried and recrystallized from hot acetonitrile to give 240 mg (50% yield) of a light cream colored solid. M.p. 332°–333° C.

NMR (TFA-d/DMSO-d$_6$, 250 MHz): 9.38 (s, 1H), 9.15 (d, J=1.0 Hz, 2H), 8.88 (d, J=6.4 Hz, 1H), 8.44 (t, J=6.4 Hz, 1H), 8.27 (d, J=9.6 Hz, 1H), 5.15 (br m, 2H), 3.65 (br m, 2H).

EXAMPLE 8

5-Fluoro-2-nitro-6-(3'-pyridyl)-N-methyl-N-(2-hydroxyethyl)aniline

A. By the method described in Example 7A, 2,4-difluoro-3-(3'-pyridyl)-nitrobenzne (1.53 g, 6.48 mmoles) in THF (25 ml) and triethylamine (1 ml) was reacted with N-methylaminoethanol (2.43 g, 32.4 mmoles) at room temperature to give 684 mg (36% yield) of a yellow solid. M.p. 140°–142° C.

NMR (CDCl$_3$, 250 MHz): 8.65 (d of d, J=4.0 Hz and 1.0 Hz, 1H), 8.59 (d, J=1.98 Hz, 1H), 7.78 (d of d, J=10.7 and 4.0 Hz, 1H), 7.72 (d of q, J=8.0 Hz, 1H), 7.45 (d of d, J=8.0 and 4.0 Hz, 1H), 6.93 (d of d, J=8.0 Hz, 1H), 3.52 (q, 2H), 2.76 (t, 1H), 2.72 (s, 3H), 2.68 (t, J=6.4 Hz, 2H).

5-Fluoro-2-amino-6-(3'-pyridyl)-N-methyl-N-(2-hydroxyethyl)aniline

B. The title compound was prepared by the method of Example 7B from 5-fluoro-2-nitro-6-(3'-pyridyl)-N-methyl-N-(2-hydroxyethyl)aniline (680 mg, 2.34 mmoles) in absolute ethanol and stannous chloride dihdyrate (5 eq) at 50° C. for 30 minutes. The product is a yellow solid of m.p. 164°–165° C.

NMR (CDCl$_3$, 250 MHz): 8.65 (d of d, J=7.6 and 1.0 Hz, 1H), 8.56 (d, J=1.0 Hz, 1H), 7.64 (d of t, J=6.0 Hz, 1H), 7.38 (d of d, J=8.0 and 4.0 Hz, 1H), 6.85 (t, J=8.0 Hz, 1H), 6.76 (d of d, J=8.0 and 4.0 Hz, 1H), 3.55 (br t, 2H), 3.42 (br s, 2H), 2.74 (s, 1H), 2.65 (m, 2H), 2.62 (s, 3H).

2-[N-Methyl-N-(2-hydroxyethyl)amino-3-(3'-pyridyl)-4-fluorophenyl]amino methylene malonic acid diethyl ester C. By the method of Example 7C 825 mg (96% yield) of the title compound was prepared from 5-fluoro-2-amino-6-(3'-pyridyl)-N-methyl-N-(2-hydroxyethyl)aniline (520 mg, 1.99 mmoles) and diethyl ethoxy methylene malonate (505 mg, 2.34 mmoles). The product is a yellow solid of m.p. 99°–102° C.

NMR (CDCl$_3$, 250 MHz): 11.8 (d, J=14.4 Hz, 1H), 8.68 (d of d, J=6.7 and 1.0 Hz, 1H), 8.60 (d, J=14.4 Hz, 1H), 8.56 (m, 1H), 7.65 (br d, J=5.0 Hz, 1H), 7.42 (d of d, J=8.6 and 4.2 Hz, 1H), 7.29 (d of d, J=8.6 and 4.2 Hz, 1H), 7.02 (t, J=9.6 Hz, 1H), 4.29 (six line multiplet, J=7.0 Hz, 4H), 3.48 (t, J=7.2 Hz, 2H), 2.76 (s, 3H), 2.75 (m, 2H), 1.35 (two overlapping triplets, 6H).

2-(8-Fluoro-7-(3'-pyridyl)-1-methyl-2,3-dihydroquinoxaline-4-yl)methylene malonic acid diethyl ester D. By the method of Example 7D 750 mg (99% yield) of the title compound was prepared from 2-[N-methyl-N-(2-hydroxyethyl)amino-3-(3'-pyridyl)-4-fluorophenyl] amino methylene malonic acid diethyl ester (790 mg, 1.83 mmoles), triphenylphosphine (720 mg, 2.75 mmoles) and ethyl azodicarboxylate (480 mg, 2.75 mmoles). The product is a yellow oil.

NMR (CDCl$_3$, 250 MHz): 8.58 (br s, 1H), 8.58 (d of d, J=4.0 and 1.0 Hz, 1H), 7.98 (s, 1H), 7.79 (d of q, J=7.8 Hz, 1H), 7.38 (d of d, J=7.8 and 3.9 Hz, 1H), 7.02 (d of d, J=9.8 and 4.0 Hz, 1H), 6.82 (t, J=8.2 Hz, 1H), 4.28 (m, 4H), 3.43 (t, J=4.0 Hz, 2H), 3.16 (t, J=4.0 Hz, 2H), 2.30 (s, 3H), 1.32 (m, 6H).

9-Fluoro-10-(3'-pyridyl)-1-methyl-7-oxo-2,3-dihydro-7H-pyrido (1,2,3-d,e) quinoxaline-6-carboxylic acid ethyl ester E. The title compound (448 mg, 84% yield) was prepared by the method of Example 7E as a light tan solid of m.p. 281°–285° C. from 2-(8-fluoro-7-(3'-pyridyl)-1-methyl-2,3-dihydroquinoxaline-4-yl) methylene malonic acid diethyl ester (600 mg, 1.45 mmoles).

NMR (CDCl$_3$, 250 MHz): 8.72 (br s, 1H), 8.66 (br d, J=3.9 Hz, 1H), 8.29 (s, 1H), 7.84 (d of q, J=9.9 Hz, 1H), 7.70 (d, J=9.9 Hz, 1H), 7.68 (m, 1H), 4.38 (q, J=6.4 Hz, 2H), 4.13 (t, J=4.0 Hz, 2H), 3.44 (t, J=4.0 Hz, 2H), 2.44 (s, 3H), 1.41 (t, J=6.4 Hz, 3H).

9-Fluoro-10-(3'-pyridyl)-1-methyl-7-oxo-2,3-dihydro-7H-pyrido [1,2,3-de]quinoxaline-6-carboxylic acid.
(R$_1$=hydrogen; R$_2$=3-pyridyl; X=); R$_4$=hydrogen; n=1)

F. A 110 mg (31% yield) sample of 9-fluoro-10-(3'-pyridyl)-1-methyl-7-oxo-2,3-dihydro-7H-pyrido[1,2,3-d,e]quinoxaline-6-carboxylic acid was prepared from 9-fluoro-10-(3'-pyridyl)-1-methyl-7-oxo-2,3-dihydro-7H-pyrido[1,2,3-de]quinoxaline-6-carboxylic acid ethyl ester by the method of Example 5F. M.p. 353°–354° C. with decomposition (CH$_3$CN).

NMR (DMSO-d$_6$/TFA-d, 250 MHz): 9.27 (s, 1H), 9.20 (s, 1H), 9.01 (d, J=7.2 Hz, 1H), 8.94 (d, J=7.2 Hz, 1H), 8.36, (d of d, J=8.2 and 6.0 Hz, 1H), 7.99 (d, J=7.94 Hz, 1H), 4.85 (br s, 2H), 3.79 (br s, 2H).

The following Table sets out the in vitro anti-bacterial activity of compounds of the invention and compares them with Rosoxacin, a prior art compound according to U.S. Pat. No. 3,753,993.

TABLE

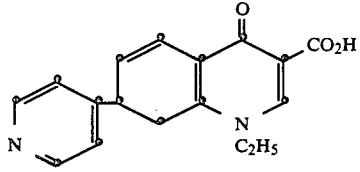

Rosoxacin

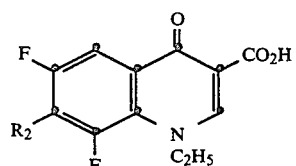

| | Facultatively anaerobic | | | Obligately anaerobic | |
|---|---|---|---|---|---|
| | S. | | | | |
| | E. coli | choler. | St. aureus | B. fragilis | F. necro. |
| Rosoxacin | 0.78 | 0.78 | 0.78 | 25 | 25 |
| R$_2$ = 4-pyridyl | 0.2 | 0.2 | 0.05 | 0.39 | 0.39 |
| R$_2$ = 3-pyridyl | 0.2 | 0.2 | 0.05 | 0.39 | 0.78 |
| R$_2$ = 6-quinolyl | 0.39 | 0.39 | 0.003 | 0.39 | 0.78 |

The advantageous bacterial activity of the compounds of the invention is particularly clear with respect to the obligately anaerobic bacteria, and with respect to gram positive bacterium St. aureus.

We claim:
1. A compound selected from those of the formula:

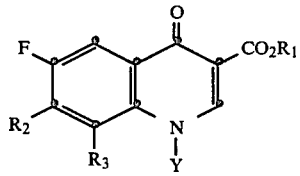

wherein
R$_1$ is hydrogen, a pharmaceutically acceptable cation or alkyl of 1 to 3 carbon atoms;
Y is selected from the group consisting of alkyl and haloalkyl of 1 to 3 carbon atoms, allyl, vinyl, cyclopropyl, hydroxyethyl, phenyl, 4-hydroxyphenyl and 4-fluorophenyl;
R$_2$ is 3-pyridyl or 4-pyridyl which may be substituted by one or two substituents selected from the group consisting of fluoro, chloro, hydroxy, alkoxy of 1 to 4 carbon atoms, amino, dialkylamino of 2 to 8 carbon atoms, hydroxyalkyl of 1 to 6 carbon atoms, aminoalkyl of 1 to 6 carbon atoms; 5-pyrimidyl, or 6-quinolyl, and
R$_3$ is fluoro;
and the acid addition salts thereof when R$_1$ is hydrogen.

2. A compound as claimed in claim 1 wherein R$_1$ is hydrogen or a pharmaceutically acceptable cation.

3. A compound as claimed in claim 2 wherein R$_1$ is sodium or potassium.

4. A compound as claimed in claim 2 wherein Y is ethyl.

5. A compound as claimed in claim 4 wherein said compound is selected from the group consisting of 6,8-difluoro-7-(4-pyridyl)-1-ethyl-1,4-dihydroquinol-4-one 3-carboxylic acid and 6,8-difluoro-7-(3-pyridyl)-1-ethyl-1,4-dihydroquinol-4one 3-carboxylic acid.

6. A compound as claimed in claim 4 wherein said compound is selected from the group consisting of 6,8-difluoro-7-(4-pyridyl)-1-ethyl-1,4-dihydroquinol-4-one 3-carboxylic acid sodium salt, 6,8-difluoro-7-(3-pyridyl)-1-ethyl-1,4-dihydroquinol-4-one 3-carboxylic acid sodium salt, 6,8-difluoro-7-(5-pyrimidyl)-1-ethyl-1,4-dihydroquinol-4-one 3-carboxylic acid, and 6,8-difluoro-7-(6-quinolyl)-1-ethyl-1,4-dihydroquinol-4-one 3-carboxylic acid.

7. A compound as claimed in claim 2 wherein Y is fluoroethyl.

8. 6,8-Difluoro-7-(6-quinolyl)-1-fluoroethyl-1,4-dihydroquinol-4-one 3-carboxylic acid, in accordance with claim 7.

9. An antibacterial composition comprising a compound as claimed in claim 1 and a pharmaceutically acceptable carrier.

10. A method for treating a host affected by bacterial disease which comprises administering to said host an antibacterially effective amount of a compound as claimed in claim 1.

11. A composition effective against Staphylococcus aureus comprising 6,8-difluoro-7-(4-pyridyl)-1-ethyl-1,4-dihydroquinol-4-one 3-carboxylic acid or 6,8-difluoro-7-(3-pyridyl)-1-ethyl-1,4-dihydroquinol-4-one 3-carboxylic acid and a pharmaceutically acceptable carrier.

12. A composition effective against Staphylococcus aureus comprising 6,8-difluoro-7-(6-quinolyl)-1-ethyl-1,4-dihydroquinol-4-one 3-carboxylic acid and a pharmaceutically acceptable carrier.

* * * * *